(12) United States Patent
Park et al.

(10) Patent No.: US 9,281,170 B2
(45) Date of Patent: Mar. 8, 2016

(54) SELECTIVE ION MOBILITY SPECTROMETER FORMED FROM TWO CONSECUTIVE MASS SELECTIVE FILTERS

(71) Applicant: Bruker Daltonik GmbH, Bremen (DE)

(72) Inventors: Melvin Andrew Park, Billerica, MA (US); Desmond Allen Kaplan, Billerica, MA (US); Mark Ridgeway, Bremen (DE)

(*) Notice: Subject to any disclaimer, the term of this patent is extended or adjusted under 35 U.S.C. 154(b) by 0 days.

(21) Appl. No.: 14/540,197

(22) Filed: Nov. 13, 2014

(65) Prior Publication Data

US 2015/0069228 A1    Mar. 12, 2015

Related U.S. Application Data

(62) Division of application No. 13/094,128, filed on Apr. 26, 2011, now Pat. No. 8,941,054.

(51) Int. Cl.
*H01J 49/00* (2006.01)
*H01J 49/06* (2006.01)
*G01N 27/62* (2006.01)

(52) U.S. Cl.
CPC .............. *H01J 49/06* (2013.01); *G01N 27/622* (2013.01); *G01N 27/624* (2013.01)

(58) Field of Classification Search
CPC ................... G01N 2015/0003; G01N 27/622; G01N 27/624
USPC .................................. 250/281, 282, 285, 286
See application file for complete search history.

(56) References Cited

U.S. PATENT DOCUMENTS

| | | | |
|---|---|---|---|
| 2002/0014586 A1* | 2/2002 | Clemmer | 250/287 |
| 2006/0027746 A1* | 2/2006 | Guevremont et al. | 250/292 |
| 2008/0203290 A1* | 8/2008 | Fernandez de la Mora et al. | 250/282 |
| 2009/0134321 A1* | 5/2009 | Hoyes | 250/282 |

* cited by examiner

*Primary Examiner* — Nicole Ippolito
*Assistant Examiner* — Jason McCormack
(74) *Attorney, Agent, or Firm* — Benoit & Cote, Inc.

(57) ABSTRACT

Ions with a predetermined range of ion mobilities are produced by filtering input ions with at least two consecutive ion mobility high pass and/or low pass filters. Each ion mobility filter is formed by entraining ions in a moving gas and applying a DC electric field to the ions which causes the ions to move in a direction opposite to the gas flow. An ion mobility high pass filter is formed when the DC electric field drives the ions against the flow of gas, whereas an ion mobility low pass filter is formed when a the gas flow drives entrained ions against an DC electric field barrier.

12 Claims, 3 Drawing Sheets

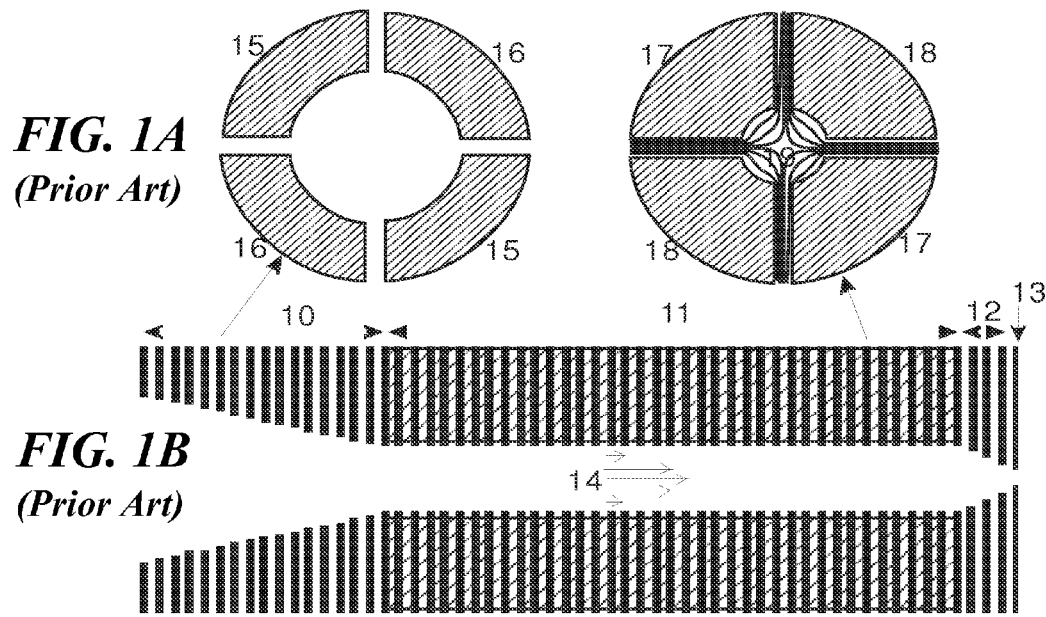
FIG. 1A (Prior Art)
FIG. 1B (Prior Art)
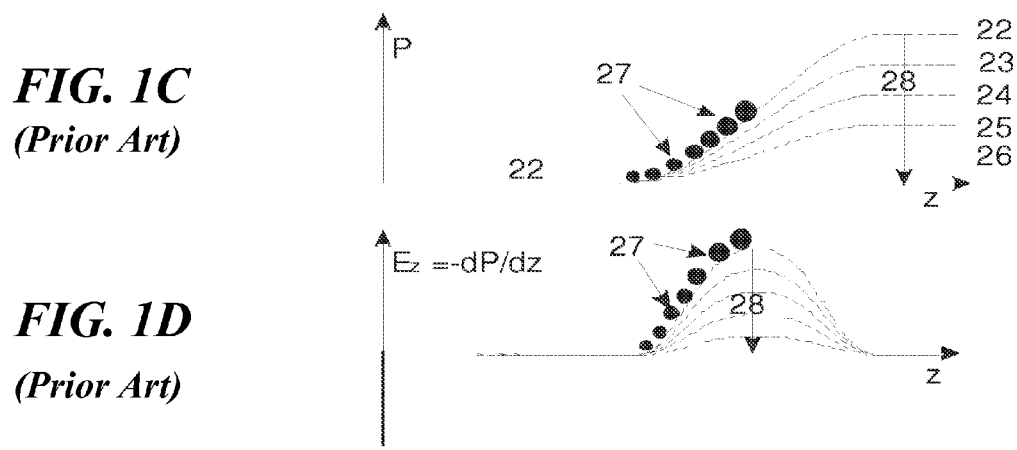
FIG. 1C (Prior Art)
FIG. 1D (Prior Art)

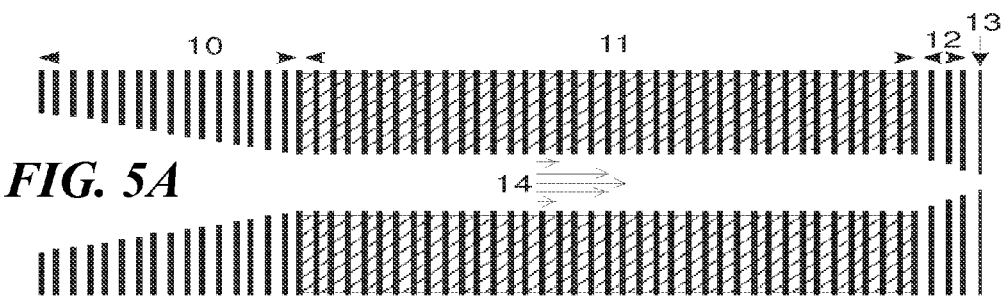
*FIG. 5A*
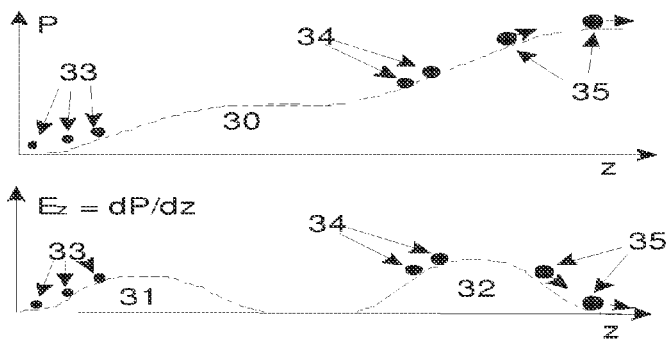
*FIG. 5B*
*FIG. 5C*
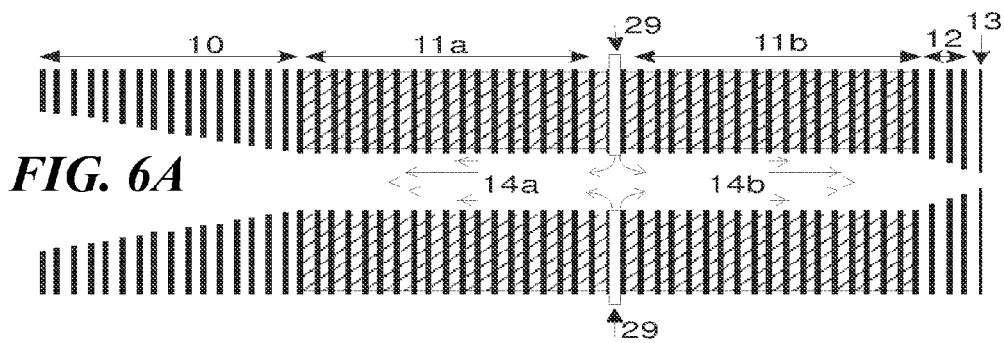
*FIG. 6A*
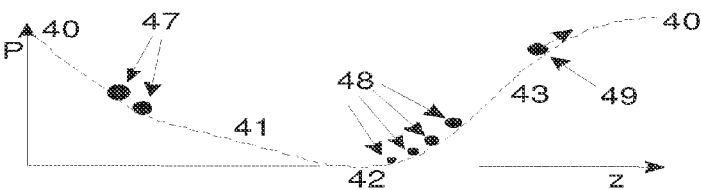
*FIG. 6B*
*FIG. 6C*

SELECTIVE ION MOBILITY SPECTROMETER FORMED FROM TWO CONSECUTIVE MASS SELECTIVE FILTERS

BACKGROUND

The invention relates to the selection of ions of a predetermined range of mobilities, preferably for being analyzed by mass spectrometry. Mass spectrometers can only ever determine the ratio of the ion mass to the charge of the ion. Where the terms "mass of an ion" or "ion mass" are used below for simplification, they always refer to the ratio of the mass m to the dimensionless number of elementary charges z of the ion. This charge-related mass m/z has the physical dimension of a mass, but it is often also called "mass-to-charge ratio", although this is incorrect with regard to the physical dimension. The term "ion species" shall denote ions having the same chemical formula, the same charge and the same three-dimensional structure. Ion species generally comprise all ions of an isotope pattern containing ions of slightly different masses, but virtually the same mobilities.

Different kinds of isomers are known for bioorganic molecules: isomers related to the primary structure (structural isomers) and isomers related to the secondary or tertiary structure (conformational isomers). These isomers have different geometrical forms but exactly the same mass. It is therefore impossible to differentiate between them on the basis of their mass. Some information as to the structure can be obtained from fragment ion mass spectra; however, an efficient and certain way to recognize and distinguish such isomers is to separate their ions according to their different mobilities.

Nowadays, the mobility of ions is often measured via their drift velocities in a drift region under the influence of an homogeneous electric field along the drift region. The drift region is filled with an inert, stationary gas (such as helium, nitrogen or argon). The ions of the substance under investigation are pulled through the gas by means of the electric field, which is produced by suitable DC potentials applied to ring electrodes arranged along the drift region. The large number of collisions with the gas molecules results in a constant drift velocity $v_d$ for each ion species which is proportional to the electric field strength E: $v_d = \mu \times E$. The proportionality factor $\mu$ is called the "ion mobility" of the ion species. The ion mobility $\mu$ is a function of the gas temperature, gas pressure, type of gas, ion charge and, in particular, the collision cross-section of the ions.

Isomeric ions with the same charge-related mass m/z but different collision cross-section have different ion mobilities in a gas of the same temperature, pressure and type. The Isomer with the smallest geometric dimension exhibits the greatest mobility compared to other isomers and therefore the highest drift velocity through the gas. Unfolded protein ions undergo more collisions than tightly folded proteins. Protein ions which are unfolded or partially folded therefore arrive at the end of the cell later than strongly folded ions of the same mass. Structural isomers, for example proteins with glycosyl, lipid or phosphoryl groups at different sites, also have different collision cross-sections, which allow them to be distinguished by measuring their ion mobility.

In chemical and biological research, it has become more and more important to have knowledge about the folding structures of bioorganic ions, which can be identified via their mobility. Therefore devices to measure the mobility of ions have been incorporated into mass spectrometers, in particular, in order to combine the measurements of the charge-related mass of ions with the measurement of collision cross-sections. The folding structures determine the mechanism of action and thus the function of the molecules in the living organism; different foldings can signify normal or abnormal functioning of biopolymers in biosystems, and hence health or disease of tissue parts or even whole organisms.

A number of academic research groups have coupled ion mobility spectrometers with mass spectrometers. A pressure in the range of several hectopascals has been adopted almost universally in the drift region; the drift region for higher mobility resolutions measures up to four meters and more, and electric field strengths of 2,000 volts per meter and more are applied. In this pressure range, the drifting ions appear to form hardly any complexes with other substances, so the mobilities of the ion species can be measured without interferences, unlike mobility measurements at atmospheric pressure. But in the long drift regions, the ions also diffuse radially over long distances, and therefore quite large diameters have to be chosen for these drift regions.

The ions are usually introduced into the drift region by pulsing a shutter grid at the entrance of the drift region to form ion clouds, having the shape of thin slices, which are pulled through the drift region by the electric field. In the gas of the drift region, these ion clouds are subject to diffusion, caused by collisions statistically distributed in terms of spatial directions and kinetic energies due to the molecular Brownian motion. The diffusion takes place in all directions from the cloud, thus also in radial direction to the drift direction. The gas in the drift region is sometimes kept at temperatures of between about 150 and 300 degrees Celsius, but can also be cooled down for special experiments.

The resolving power of a ion mobility spectrometer is defined as $R_{mob} = \mu/\Delta\mu = v_d/\Delta v_d$, where $\Delta\mu$ is the width of the ion signal of the mobility $\mu$ at half height, measured in units of the mobility, and $\Delta v_d$ is the correspondent difference in drift velocity $v_d$. The resolving power $R_{mob}$ is influenced predominantly by the diffusion broadening of the ion clouds, particularly for long drift regions and high electric field strengths; all other influences, such as the space charge, tend to be negligibly small. The part of the resolving power determined by the diffusion broadening is given by the equation $$R_d = \sqrt{\frac{zeEL_d}{kT\ln 2}},$$

where z is the number of unbalanced elementary charges e of the ions, E the electric field strength, $L_d$ the length of the drift region, k the Boltzmann constant and T the temperature of the gas in the drift region. A high mobility resolution can thus only be achieved by means of high field strengths E, long drift regions $L_d$, or low temperatures T. The part $R_d$ of the resolving power that is given by the diffusion is not dependent on either the type or pressure of gas in the drift region; the mobility $K_0$ itself, however, does depend not only on the temperature, but also on the pressure and type of gas.

Compared to the numerical values for mass resolutions in mass spectrometry, the mobility resolutions which can be achieved in practice are generally very low. The first commercial ion mobility spectrometer for bioorganic ions has a mobility resolution of only $R_{mob}=40$. With a mobility resolution of $R_{mob}=40$, two ion species whose collision cross-sections differ by only five percent can be well separated into two peaks.

Only highly specialized academic working groups have, as yet, been able to achieve significantly higher mobility resolutions than $R_{mob}=100$, in rare individual cases up to $R_{mob}$=200, with long drift lengths roughly between two and six meters and field strengths between 2,000 and 4,000 volts per meter, making it possible to differentiate between ion species whose mobilities differ by only one to three percent. Ion mobility spectrometers with a resolution above $R_{mob}$=100 shall be called "high resolution" here.

In long mobility drift regions, the transverse diffusion widens the ion clouds broadly. Therefore, longer drift regions must also have a large diameter so that the ions do not touch the enclosure of the drift region. A well established method is to guide the ions back to the axis of the drift region after they have passed through a part of the drift region, about two meters, for example. This is done using so-called "ion funnels". These consist of a larger number of parallel ring diaphragms, spaced apart from each other in the order of millimeters. The inner diameter of the diaphragm's aperture taper continuously from the diameter of the drift region, 30 to 40 centimeters, for example, down to a few millimeters and thus form a funnel-shaped enclosed volume. The two phases of an RF voltage, usually of several megahertz and between a few tens of volts and one hundred volts, are applied alternately to the apertured diaphragms, thus generating a pseudopotential which keeps the ions away from the funnel wall. An axial DC voltage gradient is superimposed on the RF voltage generating a DC electric field along the funnel. This electric field pushes the ions slowly towards the narrow exit of the funnel and through it. The ion funnel does not measurably reduce the mobility resolution of a long drift region.

Ion funnels are not only used to guide the ions back to the axis of the drift regions in ion mobility spectrometers; they are also used in mass spectrometers in general to gather the ions from larger ion clouds and to thread these ions into narrow ion guides. Such ion funnels are often found in mass spectrometers with electrospray ion sources; the ions generated outside the vacuum system are transferred, together with a curtain gas, through inlet capillaries into the vacuum system, where they are captured by ion funnels and freed of most of the curtain gas. Some mass spectrometers even contain two such ion funnels, placed in series, in order to move the ions quickly from regions with higher pressure of several hectopascals at the end of the inlet capillary to regions with lower pressure of less than $10^{-2}$ pascal.

High-resolution time-of-flight mass spectrometers with orthogonal injection of the ions (OTOF-MS), in particular, have proven successful for combinations of mobility spectrometers with mass spectrometers. For such combinations, the common high-resolution ion mobility spectrometers of the drift type have the disadvantage of being several meters long. For the construction of small, high-resolution mobility analyzers, one therefore has to look for a solution which shortens the overall length but does not diminish the mobility resolution.

In document U.S. Pat. No. 7,838,826 B1 (M. A. Park, 2008), an ion mobility spectrometer is presented, the size of which amounts to about ten centimeters only. It is based upon a gas flow driving ions against and over an electric counter-field barrier inside a modified ion funnel of a time-of-flight mass spectrometer. Since the publication of this device, ion mobility resolutions in excess of $R_{mob}$=100 have already been achieved with this small spectrometer. Considerably higher resolutions can be expected by future improvements.

Ion mobility spectrometers with moving gases and electric barriers date back to the year 1898, when J. Zeleny published an article entitled "On the Ratio of the Velocities of the Two Ions produced in Gases by Rontgen Radiation; and on some Related Phenomena", in Philosophical Magazine, No. 46, pp. 120-154. Zeleny generated ions between two parallel grids producing a homogeneous electric field and let a broad laminar flow of gas pass through the two parallel grids in a direction normal to the grids, counteracting the electric field produced between the grids. By changing the electric field, he could separate ions by their different mobilities. Since then, several patents and patent applications were published, using the principle of gas flows for the measurement of ion mobilities; in most cases, however, driving ions by electric fields of varying strengths against a moving gas. For none of these ion mobility spectrometers, however, resolutions near to $R_{mob}$=100 have been reported.

The apparatus of M. A. Park, as described in U.S. Pat. No. 7,838,826 B1, and the potential and field profiles for its operation are schematically illustrated in FIGS. 1A to 1D. FIG. 1B shows, how the parts (10) and (12) of a quadrupolar funnel, open to gas movement between the electrodes, are separated by a closed, tube-like quadrupole device (11) shown in FIG. 1A, which is vertically segmented into slices of thin electrodes (17, 18) arranged around an axis (denoted as the z-axis) with a circular central opening forming the tube. The electrodes are separated by insulating material closing the gaps. FIG. 1A shows the shape of the electrodes of the funnel (15, 16) in a direction normal to the z-axis and the shape of the electrodes that form quadrupole tube (17, 18) in a direction normal to the z-axis, the latter with equipotential lines of the quadrupolar field inside the tube. A differential pumping system of a mass spectrometer (not shown), surrounding the ion mobility spectrometer, is designed to cause a gas to flow through the tube of part (11) in a laminar way, so that the gas flow assumes the usual parabolic velocity profile (14). Ions, which enter the first part (10) of the funnel together with the gas, are collisionally focused into the axis of the tube.

FIGS. 1C and 1D show different DC potential profiles (22 to 26) along the z-axis of the tube, and corresponding barriers $E_Z$ of the electric counter field, respectively. The operation of the ion mobility spectrometer will be described by the sequence in which the DC potential profiles are supplied. The operation starts with a filling process. The steepest potential profile (22) is generated, producing the highest electric field barrier, collecting ions of all ion mobilities. The ions (27) are blown by the gas flow against the field barrier and are stopped there because they cannot surmount the field barrier. Ions with high mobility gather at the foot of the barrier, ions with low mobility gather near the summit, as symbolically indicated by the smaller and larger cross sections of the ions (27). When a suitable number of ions have been collected, the supply of further ions is stopped; for instance, by reversing the direction of the DC field within the ion funnel (10). Then, to acquire a spectrum, the potential profile (22) is lowered in height continuously in a scan (28), through potential profiles (23) to (26), resulting in a decrease of the electric barrier. During the scan, ions of higher and higher mobilities (smaller and smaller cross sections) can surmount the decreasing summit of the barrier, exit the spectrometer and be measured by an ion detector, favorably by a mass spectrometer. The measured ion current curve reflects directly the ion mobility spectrum. This device is denominated a "TIMS", or "trapped ion mobility spectrometer".

With this instrument, ion mobility resolution $R_{mob}$ increases with increasing pressure, at least up to a few hectopascal, with increasing gas flow plus barrier height, and with decreasing scan speed. The device turns out to be at least as good as drift tubes of about one to two meters in length with stationary gas as described above.

Because only a moderate amount of ions is trapped in each analyzing cycle, only a limited number of ions of each mobility is available in each single scan, in most cases not enough for a thorough investigation of ions of a selected mobility in a mass spectrometer, for instance, by the generation of fragment ion spectra. There is still a need to collect more ions of a selected mobility, or to produce a constant current of ions with a selected mobility, for example by a mobility filter.

It should be mentioned here, that there are other types of short ion mobility spectrometers using gas flows. Document US 2010/0,090,102 A1(O. Raether et al, 2008) describes, how a freely expanding gas flow from a small opening can be used to drive entrained ions over an electrical barrier within an ion funnel. In document GB 2473723 A (J. Franzen, 2009), an apparatus is presented which generates a supersonic gas flow by a Laval nozzle, the supersonic gas flow driving entrained ions over an electrical barrier. In this case, the supersonic gas flow with entrained ions is not enclosed by any radially confining field, particularly not by an RF multipole field.

SUMMARY

The invention is based on the insight that all ion mobility measuring devices with electrical forces and counteracting gas flows act either as ion mobility high pass or low pass filters, each separating ions by their mobilities into those which pass the device and those which are held back. If an electric force generated by a DC potential profile or by an RF pseudopotential profile drives the ions in the direction of the original ion current from the ion source against a gas flow, a mobility high pass filter for ions with smaller cross sections than a limit is produced. If the gas flow drives entrained ions in the original direction of the ion current against an electrical barrier, either a DC electric barrier or an RF pseudofield barrier generated by an RF pseudopotential, a mobility low pass filter for ions of larger cross sections than a limit is produced.

In accordance with the principles of the invention, at least two consecutive mobility high pass and/or low pass filters are used for the selection of ions within a predetermined range of ion mobilities, either for the collection of many of these ions in a suitable volume between the filters, or for the generation of a constant beam of ions with predetermined mobility passing through the filters.

In a first embodiment of the invention, the gas flows in one direction only through two mobility filters, thus forming either two ion mobility low pass or two ion mobility high pass filters. If the space between the filters acts as an ion storage volume, e.g. formed by an enveloping RF multipole field, these filters cause ions within a predetermined range of mobilities to collect between the two filters. The collected ions in the selected mobility range may finally be investigated in more detail, e.g. by a highly resolved mobility scan of the second filter, or by transferring these ions to a mass spectrometer for the generation and acquisition of fragment ion mass spectra.

In a second embodiment, the gas flows in the consecutive ion mobility filters do not have the same direction, thus producing at least one high pass and at least one low pass filter. If the field strengths and the gas flows are adjusted correctly, ions of a selected range of mobilities can pass through both filters, thus forming a continuous current of ions with selected mobilities. These ions may be further investigated by a mass spectrometer, e.g. by acquiring spectra of fragment ions after application of a suitable fragmentation method.

By a common change of the adjustment of the consecutive filters in the second embodiment, the mobility range of the passing ions can be scanned.

BRIEF DESCRIPTION OF THE DRAWINGS

FIGS. 1A to 1D schematically illustrate design (1A and 1B) and potential and field profiles for the operation (1C and 1D) of an ion mobility spectrometer according to the state of the art, as described in U.S. Pat. No. 7,838,826 B1 (M. A. Park, 2008). The gas is flowing in tube (11) with parabolic velocity distribution (14). The operation is shown schematically by the profiles of the potential (1C) and the electric counter-field barrier (1D) and their effect on the gas-driven ions (27) with different cross sections indicated by the size of the dots.

FIGS. 5A-5C schematically exhibit, as an example for a first embodiment of the invention, a tube arrangement (FIG. 5A), a DC potential profile (30) (FIG. 5B) and the resulting two DC electric field barriers (31) and (32) (FIG. 5C) forming two consecutive ion mobility low pass filters for the collection of ions (34) of a predetermined range of mobilities between the two barriers inside a radial RF quadrupole field.

FIGS. 6A-6C schematically show an example of a second embodiment, with two opposite gas flows (14a) and (14b) inside the tube halves (11a) and (11b) (as shown in FIG. 6A), the potential profile (40) (FIG. 6B), forming the driving electric field (44) in the counteracting gas flow for the ion mobility high pass filter, and the second field barrier (46) for the ion mobility low pass filter, presented in FIG. 6C. The ions (49) form a continuous ion current with ions of selected mobility.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

As mentioned above, the invention provides devices and methods for selecting ions with predetermined mobility. Either many of these selected ions may be collected and stored for further investigations, or ions may be filtered according to their mobility, thus generating a constant beam of ions with predetermined mobility.

The invention is based on the finding that all ion mobility measuring devices with electrical forces and counteracting gas flows act either as ion mobility high pass or low pass filters, each separating ions into those which pass the device and those which are held back. It should be kept in mind that ions with higher mobilities as a rule have smaller cross sections; ions with lower mobilities have larger cross sections, and ions with larger cross sections experience larger friction forces in the gas. If the electric force drives the ions against a gas flow, the result is a mobility high pass filter; if the gas flow drives entrained ions against an electrical barrier, the result is a mobility low pass filter.

The invention provides devices and methods with consecutive mobility high pass and/or low pass filters for the selection of ions within a predetermined range of ion mobilities, either for the collection of many of these ions in a suitable volume, or for the generation of a constant beam of ions with predetermined mobility. In some embodiments of the invention, exactly two consecutive high pass and/or low pass filters are used.

In first embodiments of the invention, the gas flows in one direction only through two mobility filters, forming either two consecutive ion mobility low pass or two ion mobility high pass filters. These two filters allow for the collection of ions with selected ion mobilities between the two filters.

Figure 2:
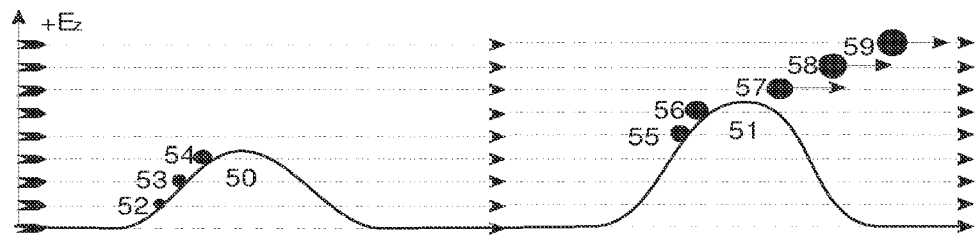
FIG. 2 depicts the operation of an inventive embodiment with two ion mobility low pass filters. A gas flow from left to right blows ions (52-59) with different cross sections against two electric field barriers (50) and (51). The selected ions (55) and (56) are collected between the two barriers.

In one of these first embodiments, the gas drives entrained ions against a first field barrier, keeping back all ions with mobilities $\mu \geq \mu_1$. This case is schematically illustrated in FIG. 2, showing the disposition of ions (52) to (59) with different mobilities, indicated by different sizes of the dots representing the ions with their cross sections. The gas drives the ions (55) to (59), that have passed the first barrier (50) against a second field barrier (51), keeping back the ions (55) and (56) with mobilities $\mu \geq \mu_2$ and thus keeping back and collecting all ions of an mobility in the range $\Delta\mu$ between $\mu_1$ and $\mu_2$ with $\mu_1 > \mu_2$. The ions (57) to (59) with $\mu < \mu_2$ pass the second barrier and disappear. To collect the ions (55) and (56), there has to be an ion storage device between the filters, e.g. by the provision of radial forces to keep the ions within the collection volume between the two barriers, such like a multipole field with its centripetally acting pseudopotential. The simplest way to generate the storage volume may be an enclosure of both filters in an RF multipole device, for instance, in an RF quadrupole system. The collected ions (55) and (56) in the mobility range $\Delta\mu$ may finally be investigated in more detail, e.g. by a highly resolved mobility scan using the second mobility filter, or by transferring these ions to a mass spectrometer for the generation and acquisition of fragment ion mass spectra.

Figure 3:
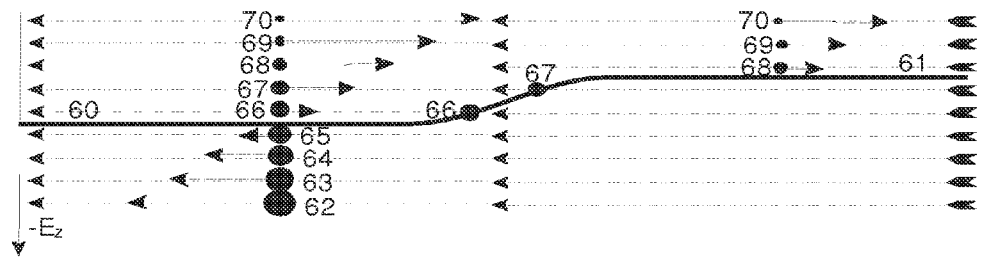
In FIG. 3, the gas blows from the right-hand site to the left-hand site, and electric forces $-E_z$ drive the ions in the direction to the right. (The electric field strength here is negative, because in this description a positive field $E_z$ always defines a counter field). Two different field strengths (60) and (61) form two different high pass filters, each separating the ions by their mobilities. The ions (66) and (67) with medium mobility are collected in between the two high pass filters.

In another of these first embodiments, the gas flow is directed towards the source of ions, forming two high pass filters, in which electric fields of adjustable strength drive the ions (62) to (70) against a constant flow of gas. This embodiment is symbolically shown in FIG. 3. In the left-hand half of the Figure, a field of strength (60) can only transport the ions (66) to (70) against the gas, and in the right-hand half, the weaker field strength (61) can only the ions (67) to (70) transport further. The ions (66) and (67) of the selected range of mobilities are collected between the two high pass filters. Again, the ions in this collection volume have to be enclosed by a suitable storage device.

In a second embodiment, the gas flows in two consecutive filters in different directions, thus producing one high pass and one low pass filter. An example is symbolically presented in FIG. 4. If field strengths and gas flows are adjusted correctly, ions (77) and (78) of a selected range of mobilities can pass both filters, thus forming a continuous current of ions with selected mobilities. In the embodiment shown, gas must be introduced between the two mobility filters, generating two gas flows in two opposing directions. In the first mobility filter, an electric field of controllable strength (71) is adjusted so that it cannot drive ions (73) to (76) with $\mu < \mu_3$ against the gas flow, thus forming a mobility high pass filter for ions (77) to (81), keeping back the ions of low ion mobility. In the second mobility filter, an electric field barrier (72) in the gas flow forms a mobility low pass filter, and only ions (77) and (78) with mobilities in the range between $\mu_3$ and $\mu_4$ can successfully pass the embodiment. These ions (77) and (78) of predetermined mobility may be further investigated by a mass spectrometer. It is even possible to scan this filter function, in order to investigate ions of more than only one mobility.

By pumping gas from the space between two filters, the direction of the two gas flows will be changed, so that, with corresponding potential profiles, a first mobility filter acts as a low pass filter, and the second as the high pass filter.

Figure 4:
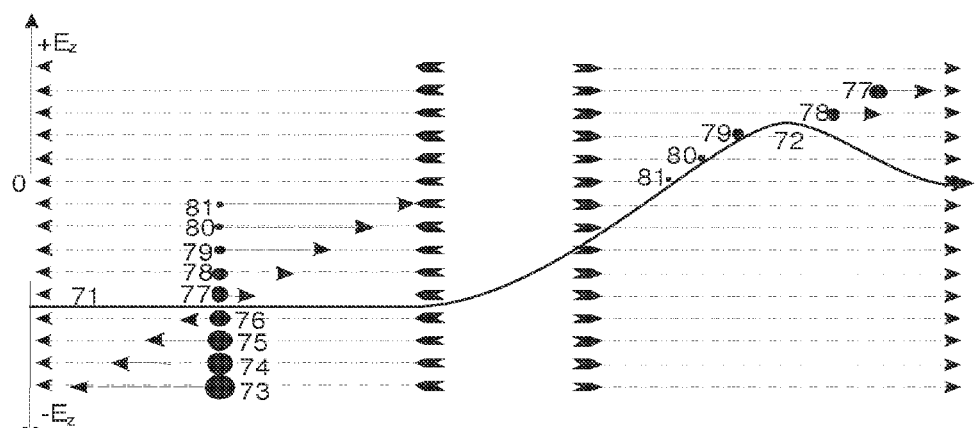
In FIG. 4, an ion mobility high pass filter (left-hand side) is combined with an ion mobility low pass filter (right-hand side), to select the ions (77) and (78), which can pass the two mobility filters in a continuous ion current and may be analyzed by a mass spectrometer.

Examples for the two embodiments symbolically depicted in FIGS. 2 and 4 are now described in more detail, based on the ion mobility spectrometer as described in document U.S. Pat. No. 7,838,826 B1 (M. A. Park, 2008), but, according to the invention, modified to form two consecutive ion mobility filters inside the spectrometer.

One arrangement of the first embodiment of the method is schematically illustrated in FIGS. 5A-5C, showing the tube (11) with unidirectional gas flow (14) in FIG. 5A, the voltage profile (30) in FIG. 5B, and the two electric barriers (31) and (32) in FIG. 5C. A pattern of electrodes at the inner wall of the tube generates both the RF quadrupole field and the DC potential profile for the DC electric field barriers. The electric field barriers form two ion mobility low pass filters for ions with mobilities $\mu < \mu_1$ and $\mu < \mu_2$, respectively. The ions (33) of highest mobility are held back by the first barrier (31), the ions (35) of lowest mobility pass the second barrier (32), and the selected ions (34) of the mobility range between $\mu_1$ and $\mu_2$ are collected and stored in the quadrupolar RF field of the tube between the two electric barriers (31) and (32) shown in FIG. 5C. These (34) ions may then be investigated in more detail, e.g. by a mobility measurement with highest resolution using the second electric field barrier.

Particularly interesting, however, is an investigation of these stored ions (34) by a mass spectrometer (not shown in the figures). The ions (34) may be transferred to a fragmentation cell of the mass spectrometer, where the ions may be fragmented by one of the well-known fragmentation processes, as, for instance, collisionally induced decomposition (CID) or electron transfer dissociation (ETD). The fragment ions are then investigated by the mass analyzer of the mass spectrometer. The ion mobility device must be arranged between ion source and analyzer of the mass spectrometer; for a fragmentation, between ion source and fragmentation cell.

An example of an arrangement for the second embodiment is schematically presented in FIGS. 6A-6C. Two gas flows (14a) and (14b) in opposite directions have to be generated by supplying gas (29) to the tube (11a, 11b) at a location near the middle. In FIG. 6C, a first electric driving field with strength (44) in the counter-flowing gas (14a) forms an ion mobility high pass filter for ions with mobilities $\mu > \mu_3$, and an electric field barrier (46) generated by the potential profile (40, 41, 42 in FIG. 6B) forms an ion mobility low pass filter in the gas flow (14b) for ions with mobilities $\mu < \mu_4$, so that ions with selected mobilities $\mu_4$–$\mu_3$ can pass continuously the two mobility filters. The two gas flows (14a) and (14b) may not have necessarily the same velocity.

In FIG. 6A, the tube (11) is now divided into two parts (11a) and (11b), and gas (29) is supplied between the two parts, generating the two gas flows (14a) and (14b). The potential profile (40, 41, 42 shown in FIG. 6B) produces the driving field (44) for ions against the gas flow (14a), forming the mobility low pass filter which continuously keeps back the ions (47) of low mobility. The part (42, 43) of the voltage profile forms the electric field barrier (46, FIG. 6C) of the mobility high pass filter, holding back the ions (48) of highest mobility, and letting pass the ions (49) of the selected mobility range. These ions form a continuous current of ions, quite different from the phase-wise ion selection of the first embodiment in a volume. The ions of this continuous current may be further analyzed by a mass spectrometer, e.g. by collection and fragmentation of these ions in a fragmentation cell, and analysis of the fragment ions by the analyzer. It has to be mentioned, that the ions which are held back in tube (11a, 11b) have to be eliminated in some way or other, either continuously by suitable means, or periodically, e.g., by periodically weakening the focusing RF voltage at the electrodes of the tube. The elimination is supported by the space charge of these ions.

The invention also comprises the corresponding selection device for ions of predetermined mobility, with a tube (11) with four rows of electrodes (17), (18) as shown in FIG. 1A along the inner wall, an RF generator to supply the rows of electrodes alternately with the phases of an RF voltage to generate the quadrupolar RF field for the collection of the ions in the tube axis, a network of resistors (not shown) connected to the electrodes (17) and (18), at least two DC voltage generators (not shown), connected to the network of resistors, generating potential profiles with at least two electric field barriers inside the tube, and means for generating at least one laminar gas flow inside the tube.

In a first embodiment of the selection device, two electric field barriers form, for ions driven by a given unidirectional gas flow, two subsequent ion mobility low pass filters for ions with mobilities $\mu<\mu_1$ and $\mu<\mu_2$ respectively. A second embodiment comprises means for the generation of two gas flows in opposite directions, and means for generating the potential profiles for a first ion mobility high pass filter for ions with mobilities $\mu>\mu_3$ and a second ion mobility low pass filter for ions with mobilities $\mu<\mu_4$.

The ion mobility selection devices are preferably mounted in a mass spectrometer, in a position between ion source and mass analyzer. If fragment spectra should be obtained, the ion mobility selection device should be mounted between ion source and fragmentation cell of the mass spectrometer.

The embodiments can be varied in many ways by any specialist in the field, e.g. by reversing the gas flow directions in the second embodiment. The gas used for the second embodiment may also replace the gas which transports the ions into the ion funnel in front of the tube. The replacing gas may not be of the same type as the transportation gas.

What is claimed is:

1. An ion mobility filter for filtering input ions to select output ions in a predetermined range of ion mobilities and output them in a first direction, comprising:
   an ion mobility high pass filter having an electric field urging ion movement in the first direction and a gas flowing in a direction opposite the first direction; and
   an ion mobility low pass filter having a gas flowing in the first direction and an electric field urging ion movement in a direction opposite the first direction;
   wherein the filters are adjusted such that the output ions that pass through them consecutively in the first direction have said predetermined range of ion mobilities.

2. An ion mobility filter according to claim 1 further comprising a coaxial RF multipole field that encloses the filters.

3. An ion mobility filter according to claim 2 further comprising a gas-tight tube within which the RF multipole field is located.

4. An ion mobility filter according to claim 3 further comprising a gas input to the tube located between the two filters, said gas input supplying each of said gas flowing in the first direction and said gas flowing in a direction opposite the first direction.

5. An ion mobility filter according to claim 1 wherein the ion mobility filter operates continuously such that the output ions represent a continuous current of ions in said predetermined range of mobilities.

6. An ion mobility filter according to claim 1 wherein the high pass filter precedes the low pass filter such that the input ions are introduced to the high pass filter, and ions exiting the high pass filter are introduced to the low pass filter.

7. A method of filtering input ions to select output ions in a predetermined range of ion mobilities that are output in a first direction, the method comprising filtering the input ions with an ion mobility high pass filter and an ion mobility low pass filter, the high pass filter having an electric field urging ion movement in the first direction and a gas flowing in a direction opposite the first direction, and the ion mobility low pass filter being having a gas flowing in the first direction and an electric field urging ion movement in a direction opposite the first direction, the filters being adjusted such that the output ions that pass through them consecutively in the first direction have said predetermined range of ion mobilities.

8. A method according to claim 7 further comprising enclosing the filters in a coaxial RF multipole field.

9. A method according to claim 8 further comprising locating the RF multipole field in a gas-tight tube.

10. A method according to claim 9 further comprising introducing gas to the tube at a position located between the two filters so as to supply each of said gas flowing in the first direction and said gas flowing in a direction opposite the first direction.

11. A method according to claim 7 wherein the ion mobility filter operates continuously such that the output ions represent a continuous current of ions in said predetermined range of mobilities.

12. A method according to claim 7 wherein the high pass filter precedes the low pass filter such that the input ions are introduced to the high pass filter, and ions exiting the high pass filter are introduced to the low pass filter.

* * * * *